(12) United States Patent
Fan et al.

(10) Patent No.: US 9,730,871 B2
(45) Date of Patent: Aug. 15, 2017

(54) ANTIPERSPIRANT/DEODORANT COSMETIC COMPOSITIONS

(71) Applicant: Colgate-Palmolive Company, New York, NY (US)

(72) Inventors: Aixing Fan, Bridgewater, NJ (US); Edward Simpson, Monmouth Junction, NJ (US); Joanna Wu, Hillsborough, NJ (US); James G. Masters, Ringoes, NJ (US)

(73) Assignee: COLGATE-PALMOLIVE COMPANY, New York, NY (US)

( * ) Notice: Subject to any disclaimer, the term of this patent is extended or adjusted under 35 U.S.C. 154(b) by 0 days.

(21) Appl. No.: 14/649,560

(22) PCT Filed: Dec. 7, 2012

(86) PCT No.: PCT/US2012/068392
§ 371 (c)(1),
(2) Date: Jun. 4, 2015

(87) PCT Pub. No.: WO2014/088586
PCT Pub. Date: Jun. 12, 2014

(65) Prior Publication Data
US 2015/0305995 A1    Oct. 29, 2015

(51) Int. Cl.
| | | |
|---|---|---|
| *A61K 8/36* | (2006.01) | |
| *A61K 8/02* | (2006.01) | |
| *A61K 8/04* | (2006.01) | |
| *A61K 8/34* | (2006.01) | |
| *A61Q 15/00* | (2006.01) | |
| *A61K 8/28* | (2006.01) | |
| *A61K 8/81* | (2006.01) | |

(52) U.S. Cl.
CPC ............ *A61K 8/361* (2013.01); *A61K 8/0229* (2013.01); *A61K 8/042* (2013.01); *A61K 8/28* (2013.01); *A61K 8/342* (2013.01); *A61K 8/8111* (2013.01); *A61Q 15/00* (2013.01); *A61K 2800/5922* (2013.01)

(58) Field of Classification Search
CPC ... A61K 8/27; A61K 8/44; A61K 8/64; A61K 2800/874; A61K 2800/58; A61Q 15/00
See application file for complete search history.

(56) References Cited

U.S. PATENT DOCUMENTS

| | | | |
|---|---|---|---|
| 5,143,718 A | 9/1992 | Bar-Shalom | |
| 5,690,919 A | 11/1997 | Rockl et al. | |
| 5,853,710 A | 12/1998 | Dehan et al. | |
| 5,976,514 A | 11/1999 | Guskey et al. | |
| 6,007,799 A | 12/1999 | Lee et al. | |
| 6,503,491 B2 | 1/2003 | Guenin et al. | |
| 6,805,855 B2 * | 10/2004 | Mattai | A61K 8/732 424/400 |
| 2008/0187503 A1 | 8/2008 | Popoff et al. | |
| 2010/0143278 A1 | 6/2010 | Banowski et al. | |
| 2011/0056268 A1 | 3/2011 | Rouse | |
| 2011/0076310 A1 * | 3/2011 | Fan | A61K 8/361 424/401 |
| 2012/0277195 A1 | 11/2012 | Banov et al. | |

FOREIGN PATENT DOCUMENTS

| | | |
|---|---|---|
| EP | 0272919 | 4/1992 |
| EP | 0764439 | 3/1997 |
| GB | EP0272919 A1 * | 6/1988 |
| WO | WO 84/04629 | 11/1984 |
| WO | WO 84/04929 | 12/1984 |
| WO | WO 96/23483 | 8/1996 |
| WO | WO 98/43605 | 10/1998 |
| WO | WO 01/87249 | 11/2001 |
| WO | WO 2005/123027 | 12/2005 |
| WO | WO 2007/114904 | 10/2007 |
| WO | WO 2008/097716 | 8/2008 |
| WO | WO 2008/144079 | 11/2008 |
| WO | WO 2009/045557 | 4/2009 |
| WO | WO 2010/081886 | 7/2010 |
| WO | WO 2011/040909 | 4/2011 |
| WO | WO 2011/040911 | 4/2011 |
| WO | WO 2011/045150 | 4/2011 |
| WO | WO 2011/050044 | 4/2011 |

OTHER PUBLICATIONS

ALMAY, 2010, "Fragrance-free anti-perspirant deodorant" Database GNPD Mintel AN: 1426891.
International Search Report and Written Opinion in International Application No. PCT/US2012/068392, mailed Sep. 17, 2013.
REVLON, 2012, "Anti-perspirant deodorant," Database GNPD Mintel AN: 1747610.
Written Opinion in International Application No. PCT/US2012/068392, mailed Nov. 12, 2014.

* cited by examiner

*Primary Examiner* — Anoop Singh
*Assistant Examiner* — Doan Phan

(57) ABSTRACT

A solid or soft solid antiperspirant/deodorant composition comprising at least one antiperspirant or deodorant active, a base component in an amount of from 2% and 15% by weight of the composition, wherein the base component is C8 to C14 fatty acid in free acid form, and a gellant, wherein the gellant comprises less than 50% by weight of the gellant stearyl alcohol. The C8 to C14 fatty acid in free acid form can be lauric acid. The C8 to C14 fatty acid in free acid form provides antibacterial properties to the compositions.

16 Claims, No Drawings

ANTIPERSPIRANT/DEODORANT COSMETIC COMPOSITIONS

BACKGROUND OF THE INVENTION

Antiperspirant and/or deodorant compositions are generally applied to an axillary region to limit perspiration and/or to limit or kill bacteria in this region. In this way, body odour caused by bacterial growth is eliminated or at least reduced.

Antiperspirants/deodorants can be delivered topically in solid or soft solid form using, for example, a stick applicator. Included in the base material of such compositions are components such as gellants which contribute to the structural integrity of the composition to achieve effective topical delivery of the composition when in use.

There is a need to provide improved antiperspirant/deodorant compositions in a more cost-effective way and/or with improved properties.

BRIEF SUMMARY OF THE INVENTION

The invention aims at least partially to meet these needs in the art.

In a first aspect, the present invention provides a solid or soft solid antiperspirant/deodorant composition comprising at least one antiperspirant or deodorant active, and further comprising a base component in an amount of between 0.5% and 15% by weight of the composition, wherein the base component is a $C_8$ to $C_{14}$ fatty acid in the free acid form, and wherein the gellant comprises less than 50% by weight of the gellant stearyl alcohol.

It has been found that incorporation of $C_8$ to $C_{14}$ fatty acids in free acid form, such as lauric acid, into antiperspirant/deodorant compositions according to the invention shows improved payout and glide properties without adverse impact on the compression or hardness properties of the antiperspirant/deodorant compositions that contain polyethylene wax as a gellant. $C_8$ to $C_{14}$ fatty acids, such as lauric acid, also have antimicrobial properties towards axillary bacteria that may help to reduce malodour generation. Because lauric acid is an inexpensive solid which is widely available and commonly used in the production of soaps and cosmetics it may be used to replace more expensive base components of the antiperspirant/deodorant compositions thereby reducing unit cost.

In a further aspect, the present invention provides an antiperspirant/deodorant product comprising a composition as described herein in the form of a stick in a suitable container.

In a further aspect, the present invention provides use of the composition as described herein as an antiperspirant or deodorant.

In a further aspect, the present invention provides a method comprising applying a composition as described herein to the axillary area of a subject.

DETAILED DESCRIPTION OF THE INVENTION

The following description of the preferred embodiment(s) is merely exemplary in nature and is in no way intended to limit the invention, its application, or uses.

The solid or soft solid antiperspirant/deodorant composition of the invention comprises at least one antiperspirant and/or deodorant active as described in further detail below. The composition further comprises an antiperspirant/deodorant base which includes a number of base components including, for example, gellants, emollients, plant oils, and other inert or functional materials including excipients and fillers. These are described in further detail below. $C_8$ to $C_{14}$ fatty acid in free acid form, such as lauric acid, is present as a base component typically in the range of from 0.5% to 15% by weight, based on the weight of the composition. Optionally, $C_8$ to $C_{14}$ fatty acid in free acid form, such as lauric acid, is present in an amount in the range of from 2% to 15%, optionally from 2% to 12% by weight of a composition, optionally from 2% to 10%, from 2% to 8%, or 2% to 6% by weight of the composition. In some embodiments the $C_8$ to $C_{14}$ fatty acid in free acid form, such as lauric acid, is present in an amount of about 2% by weight of the composition. In some embodiments the $C_8$ to $C_{14}$ fatty acid in free acid form, such as lauric acid, is present in an amount of about 5% by weight of the composition. In some embodiments, the $C_8$ to $C_{14}$ fatty acid in free acid form, such as lauric acid, is present in an amount of about 10% by weight of the composition. In certain embodiments, the $C_8$ to $C_{14}$ fatty acid in free acid form is an inexpensive material, such as lauric acid, and may be used according to the invention to replace one or more of the base components of the composition such as the gellants and/or emollients without adversely affecting the compression or hardness properties thereof. In certain embodiments, the $C_8$ to $C_{14}$ fatty acid in free acid form is a linear, unsaturated fatty acid.

The $C_8$ to $C_{14}$ fatty acid in free acid form, such as lauric acid, does not act as a gellant for the composition as does longer chain fatty acids, such as $C_{16}$ and greater fatty acids.

In order to achieve these effects, the composition contains less than 50% stearyl alcohol as gellant by weight of the gellant, optionally, less than 5% by weight of the gellant. In certain embodiments, the composition is free of stearyl alcohol, which means that there is no more than 1 weight % of the composition of stearyl alcohol or no stearyl alcohol. In the presence of stearyl alcohol in large amounts, and in particular compositions that contain hydrocarbon of the formula $C_nH_{2n+2}$, wherein n is about 20 to about 100, and the hydrocarbon is at least 90% linear, the use of $C_8$ to $C_{14}$ fatty acid in free acid form, such as lauric acid, in the compositions results in a composition whose structural integrity is compromised and is therefore not useful as an antiperspirant/deodorant composition.

Gellants

Gellants can optionally be included in the composition. Gellants are those materials known in the art that structure the composition. Examples include, but are not limited to, waxes, a hydrocarbon wax, esters of fatty acid, triglycerides, or other cosmetically acceptable materials, which are solid or semi-solid at room temperature and provide a consistency suitable for application to the skin. Plant oils may behave as gellants, and these are discussed separately below.

In one embodiment, the gellant can be selected from any $C_{16}$ to $C_{18}$ saturated fatty acid. In one embodiment, the saturated fatty acid can be stearic acid and/or palmitic acid. In one embodiment, the saturated fatty acid is palmitic acid. The amount of fatty acid in the composition may be greater than 7 weight % up to 30 weight % of the composition. In other embodiments, the amount of fatty acid may be at least 7.5, 8, 9, 10, 11, 12, 13, 14, 15, 16, 17, 18, 19, 20, 21, 22, 23, 24, or 25 weight %. In certain embodiments, the amount of saturated fatty acid is 15 to 21 weight %. In other embodiments, the amount of saturated fatty acid is 16 to 20 weight %.

In certain embodiments, the combination of a saturated fatty acid (in particular a C16 fatty acid) in an amount of 15-21 weight % (or 16-20 weight %) with a plant oil (in particular palm kernel or coconut oil) in an amount of 12-20 weight % provides a structure with a commercially acceptable compression value, which can be at least 3000 g. In certain embodiments, the compression value of the composition is 3000 g to 10,000 g, optionally the compression value of the composition is 3000 g to 6000 g or 4000 g to 5000 g.

The hydrocarbon wax can be a hydrocarbon of the formula $C_nH_{2n+2}$, wherein n is 20-100, and the hydrocarbon is at least 90% linear. In one embodiment, the hydrocarbon is a paraffin. In another embodiment, the hydrocarbon is polyethylene/polymethylene. An example of a polyethylene can be found in U.S. Pat. No. 6,503,491. In another embodiment, the polyethylene has a weight average molecular weight in of about 300 to about 3000 and a melting point of about 50 to about 129° C. In one embodiment, the hydrocarbon is synthetically made from methylene to form a polymethylene.

Preferably, the gellant is polyethylene, polymethylene or palmitic acid. The polyethylene, polymethylene or palmitic acid may be present in the composition in an amount in the range of from 15% to 30% by weight of the composition.

Plant Oils

The composition may include plant oil. By plant oil it is meant that the oil is obtained from a plant, or the plant oil can be made by blending of oil components to obtain an oil that is substantially similar in composition to a plant oil. By substantially similar, it is meant that the manufactured oil contains at least 50 weight % (or at least 60, 70, 80, 90, 95, 98, or 99 weight %) of the components that are found in the plant oil that it is designed to mimic. The term plant oil does not include fragrances.

In certain embodiments, the plant oil has a melting point below 40° C. or below 35° C. or below 30° C.

Examples of the plant oil include, but are not limited to, palm kernel, coconut, avocado, canola, corn, cottonseed, olive, palm, hi-oleic sunflower, mid-oleic sunflower, sunflower, palm stearin, palm kernel olein, safflower, and babassu oils. In one embodiment, palm kernel oil is the selected oil. In another embodiment, coconut oil is the selected oil. In another embodiment, the plant oil is a combination of palm kernel oil and coconut oil.

In certain embodiments, the plant oil is selected to be those that contain at least 40 weight % C12-C14 fatty acids. These oils will provide stick products with greater strength at the same level of oil. In other embodiments, the oil is selected as those oils with lower amounts of unsaturation. Higher levels of unsaturation could result in undesired fragrance when the unsaturated bonds become saturated over time. In certain embodiments, the amount of unsaturated components in the oil is no more than 20, 19, 18, 17, 16, 15, 14, 13, 12, 11, or 10 weight % of the oil.

The amount of plant oil in the composition may be at least 12 weight % up to 20 weight % of the composition. In certain embodiments, the amount is greater than 13, 14, 15, 16, 17, 18, or 19 weight % in the composition. In certain embodiments, the amount of plant oil is greater than the amount of volatile silicone in the composition. In one embodiment, there is no volatile silicone in the composition. In other embodiments, the amount of plant oil is more than 10, 15, 20, 25, 30, 35, 40, 45, 50, 55, 60, 65, 70, 75, 80, 85, 90, or 95 weight % of the combined weight of plant oil and volatile silicone (if present). Optionally, the amount of palm kernel oil is from 10% to 40% by weight of the composition, optionally 25% to 35% by weight of the composition.

Other plant oils include hydrogenated vegetable oils. In one embodiment, the hydrogenated oil is hydrogenated soybean oil. In one embodiment, the hydrogenated soybean oil is almost, but not fully hydrogenated. The amount of hydrogenation is measured by the iodine value. The iodine value can be measured by ASTM D5554-95 (2006). In one embodiment, the iodine value of the hydrogenated soybean oil used herein is greater than 0 to 20. In one embodiment, the iodine value is 1 to 5. In another embodiment, the soybean oil is fully hydrogenated with an iodine value of 0. In another embodiment, the iodine value is up to 20.

In one embodiment, the plant oil includes a partially hydrogenated soybean oil having an iodine value in the range of about 75 to about 80. This partially hydrogenated soybean oil can be obtained from Cargill under the product designation S-500. Reference is made to United States Patent Publication No. 2008/0187503A1. This material has a typical fatty acid distribution shown in the table below. Amounts shown are in % by weight.

| | |
|---|---|
| C16:0 | 10.5-11.2 |
| C18:0 | 6.8-7.5 |
| C18:1 | 61-65 |
| C18:2 | 16-19 |
| C18:3 | 0-0.2 |
| Saturates | 17.5-19.5 |
| Trans | 34-39 |

In another embodiment, the plant oil includes hydrogenated castor oil (castor wax). In certain embodiments, the melting point of the castor wax is 70 to 90, or it can be 70, 80, or 90.

In one embodiment, the gellant comprises a combination of the hydrogenated soybean oil with the hydrocarbon. Hydrogenated plant oil may be present in the composition in an amount of up to about 15% by weight of the composition.

Volatile Silicone

Compositions according to the present invention can include a volatile silicone. In some embodiments, volatile silicone is excluded from the composition. In one embodiment, the volatile silicone is a volatile cyclic polydimethylsiloxane (cyclomethicone), e.g., cyclopentasiloxane. By volatile material it is meant that the material has a measurable vapor pressure at ambient temperature. Preferably, the volatile cyclic polydimethylsiloxane is cyclomethicone. Various types of cyclomethicones may be used. Illustratively, and not by way of limitation, the volatile silicones are one or more members selected from cyclic polydimethylsiloxanes such as those represented by Formula I:

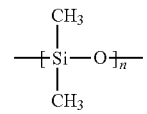

where n is an integer with a value of 3-7, particularly 5-6. Illustrative examples of suitable cyclomethicones are DC-345 and DC-245, manufactured by Dow Corning Corporation, Midland, Mich. These types include a tetramer (octylmethylcyclotetrasiloxane) and a pentamer (decamethylcyclopentasiloxane). In one embodiment, the amount of volatile silicone in the composition is greater than 0 up to 40 weight % of the composition. In another embodiment, the amount is less than 40, 35, 30, 25, 20, 15, 10, 5, or 1 weight % of the composition. In one embodiment, there is no volatile silicone in the composition. In another embodiment, there is no silicone in the composition. In another embodiment, the combined amount of the plant oil and volatile silicone is up to 50, 45, 40, 35, 30, 25, or 20 weight %.

Talc

In certain embodiments, the composition can contain talc. In one embodiment, the amount of talc in the composition is 1 to 10 weight % of the composition.

Emollients

The composition can contain emollients in any desired amount to achieve a desired emollient effect. Emollients are known in the art and are used to impart a soothing effect on the skin. Non-volatile emollients are preferable in the present invention. Classes of non-volatile emollients include non-silicone and silicone emollients. Non-volatile, non-silicone emollients include alkyl benzoate emollients such as $C_{12-15}$ alkyl benzoate. The non-volatile silicone material can be a polyethersiloxane, polyalkyarylsiloxane or polyethersiloxane copolymer. An illustrative non-volatile silicone material in the present invention is phenyl trimethicone. Non-limiting examples of emollients can be found in U.S. Pat. No. 6,007,799. Examples include, but are not limited to, PPG-14 butyl ether, PPG-3 myristyl ether, stearyl alcohol, stearic acid, glyceryl monoricinoleate, isobutyl palmitate, glyceryl monostearate, isocetyl stearate, sulphated tallow, oleyl alcohol, propylene glycol, isopropyl laurate, mink oil, sorbitan stearate, cetyl alcohol, hydrogenated castor oil, stearyl stearate, hydrogenated soy glycerides, isopropyl isostearate, hexyl laurate, dimethyl brassylate, decyl oleate, diisopropyl adipate, n-dibutyl sebacate, diisopropyl sebacate, 2-ethyl hexyl palmitate, isononyl isononanoate, isodecyl isononanoate, isotridecyl isononanoate, 2-ethyl hexyl palmitate, 2-ethyl hexyl stearate, Di-(2-ethyl hexyl) adipate), Di-(2-ethyl hexyl) succinate, isopropyl myristate, isopropyl palmitate, isopropyl stearate, octacosanol, butyl stearate, glyceryl monostearate, polyethylene glycols, oleic acid, triethylene glycol, lanolin, castor oil, acetylated lanolin alcohols, acetylated lanolin, petrolatum, isopropyl ester of lanolin, fatty acids, mineral oils, butyl myristate, isostearic acid, palmitic acid, PEG-23 oleyl ether, olelyl oleate, isopropyl linoleate, cetyl lactate, lauryl lactate, myristyl lactate, quaternised hydroxy alkyl, aminogluconate, vegetable oils, isodecyl oleate, isostearyl neopentanoate, myristyl myristate, oleyl ethoxy myristate, diglycol stearate, ethylene glycol monostearate, myristyl stearate, isopropyl lanolate, paraffin waxes, glycyrrhizic acid, hydrocyethyl stearate amide and propylene glycol butyl ether.

The composition can additionally include ionizable inorganic salts. These ionizable salts are of the form $M_aX_b$ where a=1, or 2 and b=1 or 2; M is a member chosen from $Na^{+1}$, $Li^{+1}$, $K^{+1}$, $Mg^{+2}$, $Ca^{+2}$, $Sr^{+2}$, and $Zn^{+2}$ and X is a member chosen chloride, bromide, iodide, citrate, gluconate, lactate, glycinate, glutamate, ascorbate, aspartate, nitrate, phosphate, hydrogenphosphate, dihydrogenphosphate, formate, maloneate, maleate, succinate, carbonate, bicarbonate, sulfate, and hydrogensulfate. In certain embodiments, the selected salts are chosen from NaCl and $ZnCl_2$. As will be appreciated by those skilled in the art, while it may be possible under certain circumstances to add a salt directly to a portion of the mixture during manufacturing, it is desired to add the salt as a mixture or solution of the salt in a carrier or solvent, particularly water. Of course various concentrations of the salt premix can be made.

The composition may also contain particulates which include but are not limited to talc, mica, fragrance encapsulates, or hydrophobically modified starches, such as aluminum starch octenyl succinate (MACKADERM™ ASTRO-DRY™ from McIntyre Group Ltd.). If the composition is in a liquid form and dispensed through a roll-on applicator, the average particle size of the suspended material is sized so that it can pass through the application to prevent the ball applicator from malfunctioning. Usually, the average particle size does not exceed 150 microns.

In certain embodiments, the composition may also contain as an optional ingredient at least one malodor counteracting alpha, beta-unsaturated ester or mixtures of such materials. In certain embodiments, the level of malodor counteracting composition to deliver a perceivable odor control benefit when delivered from an antiperspirant and/or deodorant composition is about 0.05 to about 0.45 weight % based on the entire composition. The alpha, beta-unsaturated ester malodor counteracting materials are incorporated within the oil phase of an antiperspirant composition.

Examples of the alpha, beta unsaturated ester include, but are not limited to:

(1) 3-phenyl-2-propenoic acid alkyl esters wherein $R^1$ is a substituent on the benzene ring and is chosen from an alkyl, an alkoxy, an aryl, or a substituted aryl. In certain embodiments, $R^1$ is chosen from H, a $C_1$ to $C_8$ alkyl, a $C_1$ to $C_8$ alkoxy, or an aryl; and $R^2$ is a subsistent group replacing the carboxylic acid hydrogen to form the ester where $R^2$ has greater than 6 carbon atoms, an aryl, or a substituted aryl group, in certain embodiments $R^2$ is a $C_6$ to $C_{12}$ alkyl or is a benzyl group; and (2) an ester of fumaric or maleic acid having linear ester carbon chains from 3-9 carbons, for example dihexyl fumarate;

(3) e-phenyl propenoic acid ester chosen from octyl methoxy cinnamate, phenylethyl cinnamate, benzyl cinnamate;

(4) an aliphatic unsaturated ester, such as dihexyl fumarate.

The composition may optionally further comprise absorbent materials such as corn starch, talc, clay, sodium polyacrylate and/or cotton fiber; and/or other materials such as fragrances, bacteriostats and/or bacteriosides, colorants, etc. Known bacteriostats include baceteriostatic quaternary ammonium compounds such as 2-amino-2-methyl-1-propanol (AMP), cetyl-trimethylammomium bromide, cetyl pyridinium chloride, 2,4,4N-trichloro-2N-hydroxydiphenylether (Triclosan), etc. and various zinc salts.

Antioxidants may be added to the composition, preferably to act as ingredient protectants and for maintenance of long-term stability of the composition. Suitable antioxidants include Tinogard, manufactured by Ciba Specialty Chemicals, Basel, Switzerland.

The antiperspirant/deodorant composition may comprise an active antiperspirant ingredient, an active deodorant ingredient or a mixture of antiperspirant/deodorant ingredients. In one arrangement, the $C_8$ to $C_{14}$ fatty acid in free acid form, such as lauric acid, constitutes at least part of the active deodorant ingredient in view of its antimicrobial properties.

Antiperspirant Active Materials

When the composition includes an antiperspirant active, any of the known antiperspirant active materials can be utilized in the composition. Antiperspirant actives include, but are not limited to, aluminum chlorhydrate, aluminum chloride, aluminum sesquichlorohydrate, aluminum-zirconium hydroxychlorides, complexes or adducts of the above-mentioned active ingredients with glycol, such as propylene glycol (for example, "Rehydrol" II from Reheis Chemical Co.), and combinations thereof. Known aluminum-zirconium salts in combination with neutral amino acids, such as glycine (e.g., aluminum-zirconium tetrachlorohydrex Gly) can also be used. Generally, any of the Category I active antiperspirant ingredients, listed in the Food and Drug Administration's Monograph on Antiperspirant Drug Products for overall-the-counter human use (Oct. 10, 1973) can be used.

In other embodiments, the antiperspirant active is an aluminum salt and/or an aluminum-zirconium salt, such as those described above, that are further stabilized by betaine and a calcium salt.

In other embodiments, the antiperspirant active, such as those described above, is selected to have a low metal to chloride ratio.

In other embodiments, the type of salt of interest, an aluminum zirconium tetrasalt or octasalt free of glycine are used wherein aluminum zirconium salt is stabilized by Betaine and has a metal to chloride ratio of about 0.9:1 to about 1.3:1 (and in other embodiments of about 0.9:1 to about 1.2:1 or about 0.9:1 to about 1.1:1). For the tetrasalt, the Al/Zr atomic ratio can be about 3.2:1 to about 4.1:1.0 and the Betaine:zirconium mole ratio can be about 0.2:1 to about 3.0:1 (or in other embodiments of about 0.4:1 to about 1.5:1). Another salt that can be used is an aluminum chloride salt buffered by Betaine, wherein the salt has a metal to chloride ratio of 0.9:1 to 1.3:1 (and in other embodiments of about 0.9:1 to about 1.2:1 or about 0.9:1 to about 1.1:1). For the octasalt the Al/Zr atomic ratio is about 6.2:1 to about 10.0:1 and the Betaine:Zr mole ratio is about 0.2:1 to about 3.0:1 (or in other embodiments of about 0.4:1 to about 1.5:1). In one embodiment, in the case of a salt that contains zirconium, the Betaine is incorporated during the synthesis of the salt so as to maximize the stabilizing effect this ingredient has (especially on the zirconium species). Alternatively, it can be post added to a glycine-free salt along with additional active phase ingredients to form a Betaine stabilized active.

Examples of commercially available glycine-free low M:Cl ratio tetrasalts and octasalts include, but are not limited to, REZAL™ AZP 955 CPG and REZAL™ AZP 885 respectively (both from Reheis Chemical Company, Berkeley Heights, N.J.).

In addition to the anti-irritation properties of Betaine, it has also been found that antiperspirant formulations preserve their fragrance stability upon ageing when the Al/Zr salt is used in association with Betaine.

Additionally, the antiperspirant active can be a calcium salt stabilized antiperspirant active.

In addition, any new ingredient, not listed in the Monograph, such as aluminum nitratohydrate and its combination with zirconyl hydroxychlorides and nitrates, or aluminum-stannous chlorohydrates, can be incorporated as an antiperspirant active. Antiperspirant actives can include, but are not limited to, the following: astringent salt of aluminum, astringent salt of zirconium, aluminum bromohydrate, aluminum chlorohydrate, aluminum dichlorohydrate, aluminum sesquichlorohydrate, aluminum chlorohydrex PG, aluminum dichlorohydrex PG, aluminum sesquichlorohydrex PG, aluminum chlorohydrex PEG, aluminum dichlorohydrex PEG, aluminum sesquichlorohydrex PEG, aluminum chloride, aluminum sulfate, aluminum zirconium chlorohydrate, aluminum zirconium trichlorohydrate, aluminum zirconium tetrachlorohydrate, aluminum zirconium pentachlorohydrate, aluminum zirconium octachlorohydrate, aluminum zirconium tetrachlorhydrex propylene glycol, aluminum zirconium trichlorohydrex Gly, aluminum zirconium tetrachlorohydrex Gly, aluminum zirconium pentachlorohydrex Gly, aluminum zirconium octachlorohydrex Gly, buffered aluminum sulfate, potassium alum, sodium aluminum chlorohydroxy lactate. In one embodiment, the antiperspirant active is aluminum chlorohydrate. In another embodiment, the antiperspirant active is aluminum zirconium tetrachlorhydrex propylene glycol.

Deodorant Active Materials

Any known deodorant active can be used. Examples of deodorant active include, but are not limited to, antimicrobial actives, alcohols, 2,4,4'-trichloro-2'-hydroxy diphenyl ether (Triclosan), benzethonium chloride, polyhexamethylene biguanides, triethylcitrate, 2-amino-2-methyl-1-propanol (AMP), cetyl-trimethylammomium bromide, cetyl pyridinium chloride, farnesol (3,7,11-trimethyl-2,6,10-dodecatrien-1-ol), bactericides, and/or bacteriostats.

The compositions as provided herein are described and claimed with reference to their ingredients, as is usual in the art. As would be evident to one skilled in the art, ingredients may in some instances react with one another, so that the true composition of the final formulation may not correspond exactly to the ingredients listed. Thus, it should be understood that the invention extends to the product of the combination of the listed ingredients.

The compositions of the present invention may be manufactured using methods known in the art. Typically, the ingredients are combined and heated to melt the components (other than inert filler), and the melted components (together with particulate inert filler) are mixed. Desirably, volatile materials, such as the fragrance materials, are incorporated in the composition in the latter stages of the mixing cycle, in order to avoid volatilization thereof. After mixing, the molten composition can be poured directly into the dispensers, after which the compositions harden into a solid, and the container is capped to preserve the product until use.

In one embodiment, the composition is a solid stick or soft solid when at ambient room temperature of about 25° C. The stick form is an example of a solid form, and the soft solid is a thickened form that may or may not be solid. The stick form can be distinguished from a soft solid in that, in a stick, the formulated product can retain its shape for extended time periods outside the package, the product not losing its shape significantly (allowing for some shrinkage due to solvent evaporation). Adjustment of amounts of gelling or thickening agents can be used in order to form a soft solid or stick.

Soft solids can be suitably packaged in containers that have the appearance of a stick, but which dispense through apertures (for example, slots or pores) on the top surface of the package. The soft solid products have also been called soft sticks or "smooth-ons", and hereinafter are generically called "soft solids".

In one embodiment, the composition is an anhydrous stick. By anhydrous it is meant that no separate water is added but there could be moisture associated with materials that are added to the composition. In certain embodiments, the amount of water is zero or less than 3, 2, 1, 0.5, or 0.1 weight % of the composition.

In one embodiment, the compression force of the composition is at least 3500 g. In other embodiments, the compression force is at least 4000 g, at least 4500 g, at least 5000 g, at least 6000 g, at least 7000 g, at least about 8000 g, at least 9000 g. In another embodiment, the compression force is 3500 g to 10,000 g. In other embodiments, the compression force is 4000 g to 6000 g or 5000 g to 6000 g In one embodiment, the composition can provide a payout of about 0.7 to about 0.9 g according to the payout test on the Payout, Glide, and Flakeoff Test Machine, which is the machine and method described in WO2009/045557. In another embodiment, the composition can provide a glide of about 0.8 to about 1.4 g according to the glide test on the Payout, Glide, and Flakeoff Test Machine. In anther embodiment, the composition can provide a flakeoff of less that about 25%. In other embodiments, the flake off is less than about 20, about 15, about 10, or about 5%. In other embodiments, the amount of flakeoff is about 1 to about 6%.

Compression strength of a stick product is measured using a Texture Analyzer Model # TA-ZT21 from Texture Technologies. The compression probe is a 19 mm square end probe. A 42.5 g (1.5 oz) antiperspirant stick is selected. The antiperspirant stick is removed from the barrel and placed in a hardness sample holder. The stick is positioned such that 2.54 cm (1 inch) of the sample, measured at the edge of the domed portion, is exposed for the test. The cover on the hardness holder is closed and the holder positioned so that the blade comes in contact with the midpoint of the exposed sample. The instrument is set to the following parameters:

Measured Force—compression (speed set at 1.0 mm/s)
Option—RETURN TO START
Distance—5.0 mm
Unit selection—grams.
The measurements to be recorded are peak force and distance required to break the stick. The higher the force reading, the stronger the stick. The longer the distance to break, the more elastic the stick.

In another embodiment, the composition is a stick that does not contain an antiperspirant active or deodorant active. In this embodiment, the stick can be formulated to be a lip balm, lipstick, or a cosmetic.

SPECIFIC EMBODIMENTS OF THE INVENTION

Example 1

Physical Properties of Polyethylene-Based Antiperspirant/Deodorant Sticks Comprising Lauric Acid The physical properties (compression, payout and glide) of antiperspirant/deodorant-like stick formulations containing various proportions of lauric acid, and a control which did not comprise lauric acid, were investigated. The distribution patterns for the residues left by the sticks on a substrate were assessed by light microscopy. The quantities of lauric acid used varied from 2% to 10% by weight of the formulation. Laurie acid was found to improve the glide properties of the formulation relative to a control. The payout was greater than or approximately equal to that of the control. Compression values were comparable to that of the control. The sticks comprising lauric acid left a more even residue that the control.

Materials and Methods

The stick formulations set out in Table 1, below, were prepared according to standard methods.

TABLE 1

| | Percentage by weight/% | | | |
|---|---|---|---|---|
| Component | Comparative formulation A | Formulation B | Formulation C | Formulation D |
| C12-C15 Alkyl benzoate | 16.8 | 16.8 | 16.8 | 16.8 |
| Hydrogenated soybean oil | 4.2 | 4.2 | 4.2 | 4.2 |
| PEG-8 distearate | 4.2 | 4.2 | 4.2 | 4.2 |
| Polyethylene synthetic wax | 10.8 | 10.8 | 10.8 | 10.8 |
| Palm kernel oil | 28.5 | 28.5 | 28.5 | 28.5 |
| AAZG-3124 (Antiperspirant active) | 22 | 22 | 22 | 22 |
| Cyclomethicone | 13.4 | 11.4 | 8.4 | 3.4 |
| Lauric acid | 0 | 2 | 5 | 10 |
| Minors | Q.S. | Q.S. | Q.S. | Q.S. |

Compression is a measure of stick hardness and is determined using a Texture Analyser (Model #TA-XT21 from Texture Technologies Corp.) fitted with a 19 mm$^2$ square end probe. The sample stick is placed in a sample holder. The sample is positioned such that 2.54 cm of the sample is exposed from the holder throughout the test. The holder is then positioned such that the probe contacts the mid-point of the exposed sample. The instrument then moves the probe at a rate of 1 mm per second for a distance of 5 mm. The peak value of the recorded compression curve is taken as the stick hardness value.

The glide and payout of each formulation are measured using the test apparatus and experimental protocols described in US Patent Application Publication No. 2011056268.

Briefly, payout measurements involve measuring the mass of the residue left by the sample stick when it is moved across the surface of a substrate in a defined manner.

The substrates used in the payout test were retained and analysed by light microscopy, in order to characterize the distribution pattern of the residue.

Glide is the coefficient of friction between the sample stick and a defined substrate. Glide testing involves moving the stick across the surface of the substrate and determining the frictional force during a defined motion using an appropriate sensor.

Results and Discussion

Physical Analysis

The results of the physical analysis of the sticks are set out in Table 2.

TABLE 2

| Formulation | Compression/g | Glide | Payout/g |
|---|---|---|---|
| Comparative formulation A | 5390 ± 60 | 0.80 ± 0.06 | 0.85 ± 0.02 |
| Formulation B | 5210 ± 190 | 0.75 ± 0.05 | 0.86 ± 0.01 |
| Formulation C | 5000 ± 100 | 0.72 ± 0.05 | 0.86 ± 0.02 |
| Formulation D | 5810 ± 140 | 0.68 ± 0.03 | 0.93 ± 0.01 |

The compression data show that the sticks comprising 2% and 5% lauric acid are of comparable hardness to the control. A slight increase in stick strength relative to the control was observed for the formulation comprising 10% lauric acid. The compositions of the present invention therefore have acceptable hardness.

The compositions comprising lauric acid displayed reduced friction coefficients relative to the control. The magnitude of the reduction in the friction coefficient was dependent on the quantity of lauric acid present. This illustrates that the compositions of the present invention have improved glide properties over conventional formulations, as represented by Comparative Formulation A.

The payouts produced by the compositions comprising 2% and 5% lauric acid were approximately equal to that of the control. Increasing the proportion of lauric acid to 10% by weight resulted in a significant increase in the payout.

Example 2

Physical Properties of Palmitic Acid-Based Antiperspirant/Deodorant Sticks Comprising Lauric Acid To demonstrate that lauric acid can be used in combination with a variety of antiperspirant/deodorant base compositions, three formulations comprising lauric acid and palmitic acid were prepared. The compression, payout and glide properties of the formulations were assessed. The lauric acid formulations were found to have improved glide, and acceptable compression and payout. Deposition patterns, as assessed by light microscopy, were found to be more homogenous.

Materials and Methods

The stick formulations set out in the table, below, were prepared according to standard methods. Compression, glide and payout for each of the formulations were assessed using the methods described in Example 1, above. The substrates used in the payout test were again retained, and investigated by light microscopy.

| Component | Comparative formulation E | Formulation F | Formulation G | Formulation H |
| --- | --- | --- | --- | --- |
| PPG-15 butyl ether | 12.5 | 11.5 | 10 | 7.5 |
| C12-C15 alkyl benzoate | 10 | 9 | 7.5 | 5 |
| Hydrogenated castor oil | 7.7 | 7.7 | 7.7 | 7.7 |
| Hydrogenated soybean oil | 2 | 2 | 2 | 2 |
| PEG-8 distearate | 3.3 | 3.3 | 3.3 | 3.3 |
| Palmitic acid | 17.8 | 17.8 | 17.81 | 17.81 |
| Palm kernel oil | 24.2 | 24.2 | 24.2 | 24.2 |
| AZP 908 (antiperspirant active) | 20 | 20 | 20 | 20 |
| Minors | Q.S. | Q.S. | Q.S. | Q.S. |
| Lauric acid | 0 | 2 | 5 | 10 |

Results and Discussion

Results of the physical analysis of the formulations are set out in the table below.

| Formulation | Compression/g | Glide | Payout/g |
| --- | --- | --- | --- |
| Comparative formulation E | 7000 ± 400 | 0.66 ± 0.03 | 0.97 ± 0.01 |
| Formulation F | 6000 ± 500 | 0.62 ± 0.04 | 0.93 ± 0.05 |
| Formulation G | 5400 ± 200 | 0.62 ± 0.02 | 0.99 ± 0.08 |
| Formulation H | 4460 ± 140 | 0.57 ± 0.03 | 1.00 ± 0.07 |

All compression values were within the acceptable range for a stick, of at least 3,500 g. The payout of the lauric acid formulations was approximately equal to that of the control. The friction coefficients of the formulations of the invention were lower than those of the control.

Comparative formulation E and Inventive Formulation H are applied to a substrate. It is observed that the use of lauric acid results in more even distribution of the crystal sizes under polarized microscope.

Example 3

Effect of Lauric Acid on the Growth of Underarm Bacteria

Laurie acid was found to inhibit the growth of *staphylococcus hemolyticus*, a common underarm bacterium.

Materials and Methods

Four simplified stick compositions, each comprising 20% stearyl alcohol gellant and 0%, 5%, 10% and 15% lauric acid, respectively, were prepared. Stearyl alcohol is not considered to be an antibacterial agent. The remainder of each stick consisted of C12-C15 alkyl benzoates, which are synthetic emollients with no antibacterial activity.

A thin layer of each formulation was coated onto an agar plate, by moving the stick across the surface of the plate. A solution of *staphylococcus hemolyticus* bacteria at 0.1 optical density as measured by UV spectroscopy was diluted by a factor of 40. 100 ml of the bacterial solution was then applied to the agar plate. The plate was incubated at 37° C. for 16 hours. The number of colonies formed on each plate was then recorded.

Results and Discussion

Stearyl alcohol was found to form sticks with very low hardness when used in combination with lauric acid. The stearyl alcohol/lauric acid sticks were also found to have very poor storage stability. Hence, this combination would not be acceptable for use in a commercial stick formulation.

The bacterial counts for each of the formulations tested and are set out in the Table below.

| Laurie acid dosage/% | Bacteria count |
| --- | --- |
| 0 | 172 |
| 5 | 120 |
| 10 | 102 |
| 15 | 49 |

The data demonstrates that lauric acid produces a reduction on the number of bacterial colonies formed. The magnitude of the effect varies with the dosage of lauric acid. In certain embodiments, the use of lauric acid as a base component will enable stick compositions comprising reduced amounts of antiperspirant/deodorant actives to be produced.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

What is claimed is:

1. A solid or soft solid antiperspirant/deodorant composition comprising at least one antiperspirant or deodorant active, a base component in an amount of from 2% to 6% by weight of the composition, wherein the base component is lauric acid in free acid form, and a gellant, wherein the gellant comprises less than 50% by weight of stearyl alcohol, and wherein the gellant further comprises at least one selected from the group consisting of polyethylene, polymethylene, and palmitic acid.

2. The composition of claim 1, wherein the lauric acid is present in an amount in the range of from 2% to 5% by weight of the composition.

3. The composition of claim 1, wherein the pH of the composition is less than 7.5.

4. The composition of claim 1, wherein the gellant is present in an amount in the range of 12% to 30% by weight of the composition.

5. The composition of claim 1, wherein the gellant comprises less than 5% by weight of the stearyl alcohol.

6. The composition of claim 1, further comprising an emollient component, which is one or more emollients selected from the group consisting of: polypropylene glycol-15 butyl ether, alkyl benzoates, cyclomethicone, and mixtures thereof.

7. The composition of claim 6, wherein the alkyl benzoates are $C_{12}$ to $C_{15}$ alkyl benzoates, which are present in an amount in the range of 5% to 17% by weight of the composition.

8. The composition of claim 6, wherein the sum of the amounts of lauric acid and the emollient component is in the range 20% to 30% by weight of the composition.

9. The composition of claim 1, further comprising at least one plant oil.

10. The composition of claim 9, wherein the plant oil is present in an amount of 10 to 40% by weight of the composition.

11. The composition of claim 9, wherein the plant oil comprises at least one hydrogenated plant oil, which is present in an amount of up to 15% by weight of the composition.

12. The composition of claim 1, which is a solid composition.

13. The composition of claim 1, wherein the composition is an anhydrous stick.

14. A method comprising applying the composition of claim 1 to the axillary area of a subject.

15. The composition of claim 1, wherein the gellant consists of polyethylene, polymethylene, or palmitic acid.

16. The composition of claim 1, wherein the gellant is free of stearyl alcohol.

* * * * *